United States Patent [19]
Sunzeri

[11] Patent Number: 5,536,382
[45] Date of Patent: Jul. 16, 1996

[54] CAPILLARY ELECTROPHORESIS ASSAY METHOD USEFUL FOR THE DETERMINATION OF CONSTITUENTS OF A CLINICAL SAMPLE

[75] Inventor: Franklin J. Sunzeri, San Jose, Calif.

[73] Assignee: Advanced Molecular Systems, Inc., San Jose, Calif.

[21] Appl. No.: 422,017

[22] Filed: Apr. 12, 1995

Related U.S. Application Data

[63] Continuation of Ser. No. 226,173, May 23, 1994, abandoned.

[51] Int. Cl.$^6$ ............ B01D 57/02; B01D 59/38; C07K 1/26
[52] U.S. Cl. ............ 204/451; 436/538; 436/546; 436/548
[58] Field of Search ............ 204/299 R, 180.1

[56] References Cited

U.S. PATENT DOCUMENTS

| | | | |
|---|---|---|---|
| 5,120,413 | 9/1992 | Chen et al. | 204/180.1 |
| 5,137,609 | 8/1992 | Manian et al. | 204/180.1 |
| 5,202,006 | 4/1993 | Chen | 204/180.1 |
| 5,228,960 | 7/1993 | Liu et al. | 204/182.8 |
| 5,348,633 | 9/1994 | Karger et al. | 204/180.1 |

OTHER PUBLICATIONS

Landers et al., "Capillary Electrophoresis: A Powerful Microanalytical Technique for Biologically Active Molecules," *Bio Techniques*, (1993) 14: 98–111.

Nielsen et al., "Separation of Antibody–Antigen Complexes by Capillary Zone Electrophoresis, Isoelectric Focusing and High Performance Size–Exclusion Chromatography," *J. Chromatography*, (1991) 539: 177–185.

Shimura & Karger, "Affinity Probe Capillary Electrophoresis: Analysis of Recombinant Human Growth Hormone with a Fluorescent Labeled Antibody Fragrment," *Anal. Chem.* (1994) 66: 9–15.

Kraak et al., "Study of Protein–Drug Binding Using Capillary Zone Electrophoresis," *J. Chromatography* (1992) 608: 257–264.

Honda et al., "Determination of the Association Constant of Monovalent Mode Protein–Sugar Interaction by Capillary Zone Electrophoresis," *J. Chromatography* (1992) 597: 377–382.

Heegaard & Robey, "Use of Capillary Zone Electrophoresis to Evaluate the Binding of Anionic Carbohydrates to Synthetic Peptides Derived from Human Serum Amyloid P Component," *Anal. Chem.* (1992) 64: 2479–2482.

*Primary Examiner*—John Niebling
*Assistant Examiner*—Edna Wong
*Attorney, Agent, or Firm*—Townsend and Townsend and Crew

[57] ABSTRACT

Methods are provided for the analysis of constituents of human biological fluids using capillary electrophoresis. A clinical sample is mixed with a labeled reagent which specifically binds the analyte of interest. Capillary electrophoresis is then used to resolve bound from unbound reagent, and the constituents quantitated by measuring directly or indirectly the amount of bound reagent.

6 Claims, No Drawings

5,536,382

CAPILLARY ELECTROPHORESIS ASSAY METHOD USEFUL FOR THE DETERMINATION OF CONSTITUENTS OF A CLINICAL SAMPLE

This is a Continuation of application Ser. No. 08/226,173, filed May 23, 1994, now abandoned.

TECHNICAL FIELD

Clinical sample analysis with capillary electrophoresis.

BACKGROUND

The need for the ability to carefully track a wide variety of analytes in clinical medicine is ever increasing. Tracking may determine the metabolism of pharmaceuticals after administration, monitor the biological status quo, determine the presence of tumor cell markers, indicate the presence of tissue damage, etc. The quantitation of analytes in complex biological samples is complicated by the; interference of other constituents which may be sticky, have analogous structures, affect the detection of the label, and the like.

Methods which utilize high pressure liquid chromatography (HPLC) are useful for small organic molecules, but may not be able to resolve complex macromolecules such as glycoproteins. In order to quantitate low concentrations of such macromolecules in complex biological samples, it is normally necessary to use a reagent, often labeled, which specifically binds the analyte. After separation of bound from unbound reagent, the amount present can be quantitated by use of the label. Immunoassays such as ELISA, RIA or solid phase immunoassay have been used in clinical analyte analysis. They have the disadvantages of being time-consuming and lacking sensitivity in the very low range of analyte concentration.

Capillary electrophoresis is a highly efficient method for the separation and detection of molecules. Conventional methods of electrophoresis are limited by the heat induced during a run. Capillary tubes, in contrast, can be run at very high voltage gradients, due to their excellent heat transfer ability. The capillary tubes used are hollow silica glass with polyimide coating on the exterior to prevent breakage. The silica wall gives a net negative charge to the inner surface. The action of an electric field on positive counterions next to the negatively charged inner wall causes the bulk flow of liquid known as electro-osmotic flow (EOF). Separation of molecules is a combined result of the effects of EOF and preferential electrophoretic mobility.

Free solution capillary electrophoresis runs the sample into a single, continuous buffer. Electrolyte buffers may be simple salts, such as borate and phosphate, or may contain additives. Micellar electrokinetic capillary chromatography adds detergents above their critical micellar concentration, thereby allowing the separation of neutral molecules on the basis of hydrophobicity. Other available methods are adapted from slab gel electrophoresis, such as isoelectric focusing, which resolves the samples by isoelectric point, or the addition of linear or cross-linked polymer to allow molecular sieving to take place. When clathrates are added, stereoisomers may be separated.

A major advantage of capillary electrophoesis is the speed in which components may be capable of being resolved, coupled with reproducibility and high level of sensitivity. It is therefore desirable to provide methods for clinical sample analysis which can take advantage of these properties.

Relevant Literature

A review of capillary electrophoresis may be found in Landers, et al. (1993) BioTechniques 14:98–111. U.S. Pat. No. 5,120,413 describes the use of a borate buffer system in the capillary zone electrophoresis of glycoproteins in clinical samples. The resolution of hemoglobin variants by capillary zone electrophoresis is disclosed in U.S. Pat. No. 5,202,006.

Nielson, et al. (1991) J. Chromatography 539:177 describe a comparison of capillary zone electrophoresis, slab gel electrophoresis and HPLC for the separation of human growth hormone and antibody complexes. Schultz and Kennedy (1993) Pittsburgh conference March 7–12 report the use of fluorescence to detect insulin in capillary electrophoresis based competitive and noncompetitive immunoassays. Shimura and Karger (1994) Anal. Chem. 66:9–15 describe the resolution of immune complexes of recombinant human growth hormone and antibody by capillary isoelectric focusing, and detected by laser induced fluorescence.

SUMMARY OF THE INVENTION

Methods are provided for the analysis of constituents of human biological fluids using capillary electrophoresis. A clinical sample is mixed with a labeled reagent which specifically binds the analyte of interest. Capillary electrophoresis is then used to resolve bound from unbound reagent, and the constituents quantitated by measuring directly or indirectly the amount of bound reagent. Assays employ competitive or noncompetitive binding methods, with or without internal assay standards.

DESCRIPTION OF THE SPECIFIC EMBODIMENTS

The constituents of clinical samples are analyzed through the use of capillary electrophoresis. Samples are mixed with a labeled binding pair member which specifically binds the analyte of interest. Capillary electrophoresis is then used to resolve bound, e.g. reagent displaced from its normal migration position, from unbound reagent, and the constituents detected. Assays may utilize competitive or noncompetitive binding methods, with or without internal assay standards.

The analyte may be any analyte having a binding site for a specific binding pair member. Of particular interest are complex biological macromolecules such as proteins, peptides, lipids and nucleic acids. In referring to specific binding pair members, it is to be understood that the two molecules have a high affinity for each other as compared to random binding. Binding pairs include antigen and antibody complexes; nucleic acid and nucleic acid binding protein complexes; enzymes and their substrates or modulators; ligands and their natural receptors, e.g. hormones and their receptors, cytokines and their receptors, sugars and lectins; and biological transport molecules and their substrates. The specific binding pair member will selectively bind to its ligand as compared to other molecules of different conformation, charge, polarity, and the like. Analyte will refer to the binding pair member which is present in the biological sample, and which is to be detected in the assay. Detector will refer to the complementary binding pair member to the analyte, and will be labeled for use in detecting the bound analyte.

In the preferred embodiment, binding pairs of labeled antibodies as detector molecules and antigen complexes are used. The antibodies will generally be monoclonal antibodies, and may be F(ab) or F(ab') fragments. The analyte may be any antigen molecule which can be specifically bound by an antibody, in most cases a protein or peptide. The amount of detector molecule added will depend on whether the assay is to be competitive or non-competitive, and on the expected physiological concentration of the analyte. The expected concentration may be empirically determined, or rely on known medical data. Quantitation of the analyte will depend on the ability to resolve uncomplexed antibody from antibody-antigen complex. Considerations will be the valency of the antibody, the presence of variant forms of the analyte in the sample, and the range of analyte concentrations which may be present in various samples.

When intact antibody, usually an IgG class, is used as a detector there are two available binding sites for antigen. There will be at least two peaks for antibody-antigen complex, one corresponding to Ab(Ag), the other to Ab(Ag)$_2$ complex. In many cases it will be preferable to use F(ab) fragments of the antibody, which have a single binding site for antigen. Interactions of the antibody Fc domain with other components of the sample may be minimized by use of F(ab) or F(ab') fragments.

A non-competitive assay is preferred, where a direct measurement is made of the amount of complex, which will be related to the amount of analyte bound to labeled antibody detector molecule. Direct assays are useful for very sensitive detection. In order to ensure that most or substantially all of the analyte is bound to antibody, an antibody concentration should be chosen which will be in excess of the analyte concentration, although one is primarily concerned with a measurable dynamic range where the amount of complex can be discriminated between the analyte increments. The concentration of antibody will be related to the anticipated maximum concentration of analyte in the sample, generally at least twice the expected maximum physiological concentration of the analyte, usually not more than about 10 mg/ml.

Direct determination will usually not be used where variation in the analyte, e.g. phosphorylation, glycosylation, ubiquitination, etc. causes multiple antibody-analyte peaks. In such cases it will be desirable to perform a subtraction assay, measuring the amount of uncomplexed antibody left after the analyte is bound. The concentration of antibody will be related to the anticipated maximum concentration of analyte in the sample, generally at least twice the expected maximum physiological concentration of the analyte, usually not more than about 10 mg/ml. Where the range of physiological concentrations is very broad, it may be desirable to run multiple assays with a range of antibody concentrations.

In some cases, a competitive assay will be used. In addition to the antibody detector molecule, a competitor to the analyte is added to the reaction mix. The competitor and the analyte compete for binding to the antibody. Usually, the competitor molecule will be labeled, and the antibody unlabeled. The measured peak will correspond to antibody-competitor complex. Competitive assays may also be used where variation in the analyte, e.g. phosphorylation, glycosylation, ubiquitination, etc. causes multiple antibody-analyte complexes to be formed, because the measured antibody-competitor peak will not be shifted by such variation. The concentration of antibody molecule will be from about 10 times the expected physiological concentration to equal the physiological concentration, more usually 2 times the expected physiological concentration. The concentration of competitor molecule will be from about 10 times the maximum anticipated analyte concentration equal concentration in order to make the most sensitive and linear range of detection.

Separation of uncomplexed antibody from antibody-antigen complex is necessary for quantitation. The conditions for capillary electrophoresis will therefore be optimized for such separation. Considerations will be resolution of a complex peak or peaks, prevention of protein sticking to the capillaries and use of stacking procedures to increase the sample loading without sacrificing resolution.

The analysis of glycosylated hemoglobin to determine glucose metabolism is of particular interest. Antigens of interest which are related to cardiovascular disease include creatine kinase (CK), particularly subtypes CK-MM and CK-MB, more particularly the CK-MB subtypes CK-MB1, CK-MB2 and CK-MB3. Other antigens which may be detected for cardiovascular profiling include prostaglandins, leukotrienes, thromboxane; prostacyclin; serotonin; coagulation factors, e.g. thrombin, fibrin, fibrinogen; Factor VIII(c); Factor XI; von Willebrand factor; tissue plasminogen activator, or other factors; complement activation factors and high and low density lipoproteins (HDL and LDL). Immune response proteins of interest include soluble HLA, class I and class II, and nonclassical class I HLA (E, F and G); soluble T or B cell surface proteins; immunoglobulins, such as IgE; erythropoietin; anglogenesis factors; adhesion molecules, in particular addressins and integrins.

Antigens expressed by tumor cells may be detected in lysates from biopsy samples, or may be detected as soluble antigens in blood, cerebrospinal fluid, urine, etc. Tumor antigens of interest include breast carcinoma; prostate specific antigen (PSA); carcinoembryonic antigen (CEA); alpha-fetoprotein (AFP); CA 125 antigen; soluble IL-2 receptor, progesterone receptor; estrogen receptor, and the like.

Cytokines may be detected through specific monoclonal antibody detectors, or by the use of their specific receptor molecule as a detector. Cytokines of particular interest include immune response modifiers such as interferons, including α-interferon, β-interferon (Betaseron) and γ-interferon; growth factors such as IL-1, 2, 3, 4, 6, 10, soluble IL2 receptor, macrophage colony stimulating factor (M-CSF), granulocyte colony stimulating factor (G-CSF), granulocyte macrophage colony stimulating factor (GM-CSF), platelet growth factors, tumor necrosis factor (TNF), tumor growth factors (TGF-α and TGF-β) nerve growth factor (NGF); macrophage inhibitory factor (MIF); macrophage activation factor (MAF) and complement factors.

Hormones may be detected through specific monoclonal antibody detectors, or by the use of their specific receptor molecule as a detector. Hormones of interest include thyroid stimulating hormone (TSH), follicular stimulating hormone (FSH), luteinizing hormone (LH), Thyroxine (T4 and T3), renin, insulin, apolipoproteins, cortisol, aldosterone, estriol, estradiol, progesterone, testosterone, dehydroepiandrosterone (DHEA) and its sulfate (DHEA-S), calcitonin, parathyroid hormone (PTH), human growth hormone (hGH), vasopressin and antidiuretic hormone (ADH), prolactin, ACTH, luteinizing hormone releasing factor (LHRH), THRH, VIP, cathecolamines (adrenaline, vanillylmandelic acid, etc.), bradykinins and corresponding prohormones.

Enzymes may be detected by specific monoclonal antibodies, or through the use of specific substrates as a detector. Enzymes of interest are those affecting cholesterol and other lipid metabolism, esterases, dehydrogenases, oxidases, hydrolases, sulphatases, cyclases, transferases, transaminases, atriopeptidases, carboxylases and decarboxylases, superoxide dismutase, etc.

The rapid detection of bacterial toxins in the blood or other biological fluids can be critical in a clinical setting.

Monoclonal antibodies may be used to detect toxins such as LPS and other gram negative toxins, Staphylococcus toxins, Toxin A, Tetanus toxins, Diphtheria toxin and Pertussis toxins. Protein antigens shed from pathogens which can be detected in the blood include hepatitis B sAg; CMV, HSV (type 1, 2 & 6), EBV, varicella zoster virus (VZV), HIV-1 $gp^{120}$ protein, HIV-2 and other retroviruses, adenovirus, rotavirus, influenzae, rhinovirus, parvovirus, rubella, measles, polio, reovirus, orthomixovirus, paramyxovirus, papovavirus, poxvirus and picornavirus, prions, protists such as plasmodia tissue factor, toxoplasma, filaria, kala-azar, bilharziose, entamoeba histolitica and giardia, and bacteria, particularly gram-negative bacteria responsible for sepsis and nosocomial infections such as E. coli, Acynetobacter, Pseudomonas, Proteus and Klebsiella, but also gram positive bacteria such as Staphylococcus, Streptococcus, etc. Meningococcus and Mycobacteria, Chlamydiae, Legionnella and anaerobes, fungi such as Candida, *Pneumocystis carinii*, and Aspergillus, and mycoplasma such as Hominis and *Ureaplasma urealyticum*.

Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Preferred are physiological samples such as blood or derivatives thereof, such as serum or plasma (hereafter "blood"). Such samples will generally be complex mixtures, where the concentration of analyte is low. The sample can be relatively small, generally being not less than about 1 µl and will generally not exceed about 500 µl, generally being in the range of about 10 to 200 µl.

In the first step, the sample may be subjected to prior treatment such as dilution in buffered medium, concentration, filtration, or other gross treatment which will not involve any specific separation. The samples may also be desalted or undergo buffer exchange by dialysis, ion exchange chromatography, etc. Amicon™ filter units (Centriprep™ or Centricon™), Microsep™ by Filtron™ or Ultrafree™ CL filtration units from Millipore™ may be useful in such treatments. For detection of non-proteinaceous analytes, the sample may be treated with proteinase to remove proteins. The analyte may also be partially purified from the sample prior to analysis. It is preferable but not required that samples be diluted prior to analysis. Usually the dilution will be not more than 1 part sample to 100 parts diluent, more usually not more than about 1 part sample to 10 parts diluent. The diluent may be any suitably buffered solution, e.g. normal saline, phosphate buffered saline, etc.

In many cases it is helpful to treat blood with anticoagulants. In the detection of analytes present in serum, the red cells and/or clotting factors will be removed prior to analysis by centrifugation, filtration, clotting, etc. For detection of proteins present in red cells, the cells may be separated from the serum component, and lysed by conventional means, i.e. addition of mild detergent, hypotonic lysis with ammonium chloride, etc.

The antibody or other detector molecule will be labeled, so as to be directly detectable, or will be used in conjunction with secondary labeled immunoreagents which will specifically bind the antibody molecule. In general the label will have a light detectable characteristic. Preferred labels for protein detector molecules such as antibodies are fluorescers, such as fluorescein isothiocyanate (FITC), rhodamine, Texas Red, phycoerythrin and allophycocyanin. Other labels of interest may include dyes, enzymes, chemiluminescers, particles, radioisotopes, biotin to bind to labeled avidin, or other directly or indirectly detectable agent. Labeled protein A and protein G affinity ligands are suitable secondary immunoreagents. A number of chemically reactive labels for coupling are available, such as sulfhydryl-reactive haloacetyl derivatives, e.g. fluorescein, rhodamine, BODIPY and coumarin iodoacetamides, eosins, erythrosin and malachite green iodoacetamides; environment and conformation-sensitive probes such as NBD and ANS derivatives, IAEDANS and pyrene thiol reagents, stilbene and Lucifer yellow, and biotinylated iodoacetamide. Maleimides further include coumarin, pyrene, eosins and biotin maleimides, as well as MIANS and stilbenedisulfonate. Miscellaneous sulfhydryl reagents include BODIPY bromomethyl derivatives, bromomethyl bimanes and coumarins, NBD halides, acryloyl derivatives, dansyl aziridines, disulfides and SAMSA fluorescein.

Amine reactive labels include isothiocyanates, e.g. FITC, rhodamine, UV excitable isothiocyanates, photosensitizers such as erythrosin, and Malachite Green isothiocyanate; succinimidyl esters and carboxylic acids, e.g. derivatives of BODIPY, coumarin, fluorescein, rhodamine, acridone, pyrene, NBD, eosins, dinitrophenyl, digoxigenin, carbazole, DABCYL, and acridine dyes; sulfonyl chlorides e.g. Texas Red, lissamine rhodamine B sulphonyl chloride; dansyl, mansyl and TNS chlorides; pyrene and anthracene sulfonyl chlorides; and chromophoric sulfonyl chlorides and reagents for modifying amines, alcohols, arginine and guanosine e.g. ATTO-TAG, fluorescamine, OPA, acyl nitriles, acid fluorides, acyl azides, Cascade Blue Acetyl azide and miscellaneous amine and alcohol reactive reagents. Other labels of interest are phycobiliproteins and their conjugates. Intercalating agents such as Hoechst Dye, Thiazole Orange and ethidium Bromide may be used for analysis of nucleic acids.

The reaction mix of sample, detector and optionally competitor will be incubated for a period of time sufficient to allow the complementary binding pair members to form complexes. The specific conditions will depend on the nature of the reactants. In the preferred embodiment, assays utilizing antibodies ks detectors will usually be incubated at a temperature in the range of about 0° C. to 65° C., more usually from about 25° C. to 42° C., preferably at about 37° C. Assays utilizing nucleic acids as detectors may be conducted at a higher temperature range, depending on the length of the probe and the ionicity of the sample dilution buffer, usually not more than about 95° C. and more usually not more than about 75° C. The incubation time will vary depending on the reaction kinetics and the temperature, usually lasting not more than about 24 hours, more usually not more than about 6 hours, and in some cases less than one hour. Analysis of time critical analytes, such as creatine kinase when testing for myocardial infarction, may require that incubation times be cut short, before complex formation has reached equilibrium. In such cases the incubation time may be less than about 1 minute, usually less than about 5 minutes, more usually less than about 15 minutes.

Samples may need to be processed before analysis. Buffers may be added in order to improve resolution. An internal control for quantitation may be added. Amplified DNA may need to be desalted prior to injection or have primers or other interfering substances removed.

Sample injection may be hydrodynamic or electrokinetic. Usually sample concentration from clinical samples will be in the range of about 1 pg analyte/ml to 1 µg analyte/ml. Injection volumes will usually range from about 1–10 nl, but may be up to 10% of the capillary volume without peak distortion. In some cases stacking procedures, based upon field differences between the running buffer and the sample buffer, will be used. A preferred method of stacking is isotachophoresis (ITP), in which a combination of two buffer systems sandwich the sample in its own buffer and all three buffers remain separated. The capillary is filled with a leading electrolyte which is more mobile than any of the sample components, the sample is injected, and the free end of the capillary is placed in the terminating electrolyte, which has a lower mobility than any of the sample components. When voltage is applied, separation occurs at the boundary region between the leading and terminating electrolytes. All of the bands travel at the same velocity and become focused. If an analyte diffuses into another zone, it will speed up or slow down, depending upon the field strength of that zone and will rejoin its own group. ITP can be used as a concentration technique before capillary zone electrohporesis or be used on its own.

Simpler but less powerful means of stacking may be based upon injecting into a water plug, into a buffer of higher ionic strength than the sample, or by power supply polarity switching immediately after injection. Injections into a higher ionic strength buffer cause ions to migrate faster because the field is proportionally higher in the sample band, until they reach the running electrolyte boundary where the field decreases. This continues until all the sample ions become concentrated in a small zone. The field then becomes homogeneous and normal electrophoresis begins. In power supply switching, electroosmotic force carries the non-analytes out of the capillary before conventional electrophoresis begins.

The capillaries will range from about 5 to 250 µm inner diameter, usually about 25 to 100 µm inner diameter, and usually about 375 µm outer diameter. They range from about 10 to 100 cm in length, depending on the length required to resolve the sample. Capillaries are fused silica, normally with an external polyimide coating, and may be internally coated. Protein molecules tend to stick to plain capillaries, so in many cases coated capillaries will be preferred. Coatings shown to be effective in prevention of protein sticking include Supelco's P series hydrophilic capillaries, and J&W Scientific DB-17, DB-1 hydrophobic coatings. Other capillary coatings of interest may be bonded, adhered, or dynamic. Bonded coatings are coupled to the wall by silation, or directly via silicon carbide-coupling. Adhered coatings include adsorbed noncrosslinked polymers such as cellulose or PEG, or adsorbed crosslinked polymers such as polyethyleneimine. Gas chromatography and liquid chromatography phases such as C2, C8 or C18 may be used to decrease protein adsorption to the wall. Bonded or adhered coatings may be hydrophobic or hydrophilic. Hydrophobic coatings include those available from J&W Scientific (DB-5, DB-Wax and CE-Wax) and coatings from Supelco (H, H1 and H2 series). Dynamic coatings may be hydrophilic polymers used to mask wall charges and decrease EOF; or surfactants to render the wall non-reactive through ionic and/or hydrophobic interactions.

Buffers may be simple salts such as phosphate, citrate or borate, or biological buffers such as tricine, MES or TRIS. Buffers effective in antibody complex separation include tricine and NaBorate, at pH ranges of 7–8. For other applications, buffers covering pH ranges from less than 2 up to 12 may be used to achieve the appropriate separations. Change in pH may change the structure or charge on the molecules of interest, and is a convenient way to alter EOF. Ionic strengths of buffers may be varied to match the conductivity of the analyte and detector. High strength buffers may be used to decrease EOF and decrease sample adsorption.

Buffer additives include detergents, clathrates, organic modifiers, metal ions, hydrogen bonding/solubilizing agents, complexing agents, and quaternary amines. Surfactants may be nonionic, zwitterionic, cationic, anionic or bile salts, used below their critical micellar concentration as wall modifiers, ion pairing reagents or solubilizing reagents. Clathrates act as chiral selectors and include cyclodextrans, crown ethers and bile salts. Organic modifiers such as 10–50% v/v methanol, acetonitrile and TFA alter chiral separations, and EOF by decreasing zeta potential. Complexing agents, such as borate complex with carbohydrates and may be useful in separations of catecholamines and carbohydrate containing molecules (see U.S. Pat. No. 5,120, 413). Quaternary amines such as CTAB may be useful for ion pairing or EOF reversal.

Modes of separation may be based upon free solution mobility in capillary zone electrophoresis, hydrophobic/ionic interactions in micellar electrokinetic capillary chromatography, size and charge in gel electrophoresis, isoelectric point in IEF, or moving boundaries in isotachaphoresis. Free solution capillary electrophoresis and isoelectric point focusing have been shown to be effective in separation of antibody-antigen complexes.

For antibody antigen complex separation utilizing free solution mobility, preferred buffer systems are simple salts or biological buffers. Voltage gradients of 100 to 1200 V/cm will be used, with run time ranging from 1 to 60 minutes, usually about 10 min.

For isoelectric focusing separation, ampholytes are added to the antibody analyte reaction mix prior to injection. The pH range of the ampholytes will depend on the specific antibody and analyte, and will range from about 2 to 10, usually from about 2.5 to 9.5. Linear polymer, e.g. acrylamide may also be added to the sample, or be present in the capillary. The range will be determined by the isoelectric point of the detector and detectoranalyte complex. A preferred buffer system for isoelectric focusing is sodium hydroxide for the catholyte and phosphoric acid for the anolyte. Voltage gradients of 500 to 700 V/cm will be used, with run time ranging from 10 to 40 minutes, usually about 20 minutes.

In some cases separations will utilize gel electrophoresis. Gels may be cross-linked or linear polymers, or agarose. Crosslinked gels will usually be polyacrylamide/bisacrylamide from 2–6% T, where $$T = \frac{\text{grams acrylamide} + \text{grams bisacrylamide}}{\text{gel volume}}$$

and from 3–6% C, where $$C = \frac{\text{bisacrylamide}}{\text{acrylamide}}.$$

Commercially available gels are 3% T, 3% C; or 5% T, 5% C. Linear polymers may be polyacrylamide at from 0.1–6% w/v, cellulose, dextran, polyethylene glycol or polyvinylalcohol at from 0.6–1.5% w/v. Agarose may be 0.05–1.2% w/v. Metal ions such as K+, Na+ and Cu+ may be added to change selectivity. Hydrogen bonding/solubilizing agents such as urea may be added to melt double stranded DNA.

For micellar electrokinetic capillary chromatography, surfactants will be added above their critical micellar concentration. The surfactants may be nonionic, zwitterionic, cationic, anionic or bile salts. Metal ions such as K+, Na+ and Cu+, or organic modifiers such as methanol, acetonitrile and TFA may be added to change selectivity.

The run temperature may be used to alter protein conformation or protein-DNA interactions. In addition it may alter peak shape and resolution, and alter viscosity. Run temperatures for resolution of antibody-antigen complexes will range from about 4° C. to 85° C., usually from about 10° C. to 40° C., preferably 20° C.

The electrophoresis run will separate the complexes of analyte/detector (or competitor/detector) from the uncomplexed reactants. The amount of complex (or uncomplexed detector) present is determined by detection of the label present on the detector for non-competitive assays, or the label on the competitor molecule for competitive assays. Labeled molecules pass by a detection window, where they are illuminated by UV and/or visible light. As the molecules pass, the amount of light transmitted at given wavelengths is detected, as a quantity of light absorbed or as fluorescence. Complexes will be identified by their mobility under the specified electrophoretic conditions, and by the amount of light transmission from the label. The transmission will appear as a peak corresponding to the position of the complex. Quantities are determined by measuring the area of the individual peaks. For some assays, it may be necessary to use a laser source for excitation of fluorescence, in order to provide sufficient sensitivity for very low levels of analytes. For enhanced detection, especially of very sharp and small fluorescent peaks, it may be necessary to increase analog to digital conversion rates from 16 to 24 or more bits.

Assay control will be used to provide a standard for quantitation. Internal standards, external standards, and where necessary a standard addition method will be used. Migration time windows and response factors (RF) will be used for effective standardization. Migration time is based upon a time window chosen to match the differential time interval between the leading and walling edges of the peak of interest. The time interval is based upon an absolute time or a percentage of the peak migration time. If the peak falls within this window, then it will be deemed to be the same peak as the peak of interest; if it falls outside this window, then it will be considered to be a different peak from the peak of interest. To compensate for migration time drift, an internal reference standard will be added to the sample to be analyzed. If this reference standard peak drifts outside the window by a specified amount, then the instrument will adjust the time windows for all the nonreference peaks. The reference window for the reference standard peak will be larger than that of the nonreference peaks to assure that the reference peak is not missed by the computer algorithm.

Calculation of response factor (RF) is used for quantitation. RF is calculated as the ratio of sample mass or concentration injected for a specific volume of sample injected, to response (height or area).

RF=amount/area External standards will be run on a parallel capillary, which necessitates highly precise injection volume control. The standard will contain a known amount of the detector/analyte complex, and the RF of the standard used as a calibration for the sample RF.

An internal standard needs to be chemically similar to the detector and stable in the assay buffers used. The internal standard will not naturally occur in the sample, must elute away from the peak(s) of interest, and be roughly the same concentration as the peak(s) of interest. Internal standards may be of the same or of different species from the sample of interest. It will be accurately calibrated and precisely added to each sample.

The amount of analyte is calculated by the equation:

$$Amount = \frac{\left(\begin{array}{c}\text{Area of the component of interest} \times \\ RF \text{ of the component of interest} \times \\ \text{Amount of internal standard}\end{array}\right)}{\left(\begin{array}{c}\text{Area of internal standard} \times \\ RF \text{ of the internal standard}\end{array}\right)}.$$

In some instances, it will be desirable to use multiple internal standards, when concentrations and/or mobilities of detector peaks are disparate.

The standard addition method (also known as the spike recovery method) will be used where the sample has a relatively large amount of interfering substances. First, the sample is analyzed with a spiked amount of calibration standard. This step is followed by analysis of the nonspiked sample. The difference in the area of the spiked and the nonspiked sample will be used for calculating the RF. Final quantitation is performed by using the internal or external standard. Quantification using both internal and external standards will be beneficial in assays where the sample matrix affects fluorescence sample quenching.

In a preferred embodiment, where an antibody detector is used to quantitate a protein or peptide analyte in blood, the external standard will usually be preformed antibody-antigen complexes run in the same percent of serum as the analyte of interest, at a concentration equivalent to the maximum anticipated analyte concentration. The internal standard will usually be labeled analyte or antibody-antigen complex with a different fluorescer at a concentration equivalent to the maximum anticipated analyte concentration.

The following examples are offered by way of illustration and not by way of limitation.

EXPERIMENTAL

I. Determination of Betaseron Concentration in Human Blood Test

Assay

A reaction mix of 100 ng/ml Betaseron™ (β-interferon) and 10% human serum in phosphate buffered saline (PBS) was pre-incubated at 37° C. for four hours. 500 ng/ml of monoclonal anti-β-interferon antibody A7 (Berlex Pharmaceuticals) labeled with FITC was added, and the reaction mix further incubated for 1 hour at 37°.

Samples were resolved by capillary electrophoresis on a AMS 2000 instrument. Capillaries were cleaned between runs for two minutes with 1N NaOH, followed by one column volume of glass distilled water, and 1 minute of washing with electrolyte buffer. Electrophoresis was run according to the following conditions: injection from 10 µl sample (5 ng labeled antibody) for 10 secs. at 0.5 bar, separation at 500 V/cm in a 25 µm inner diameter, 50 cm plain capillary with an electrolyte buffer of 50 mM tricine, pH 7.2 for 20 minutes. Alternatively, samples were run at: injection of 10 µl sample (5 ng labeled antibody) for 5 secs. at 0.1 bar; separation at 300 V/cm in a 50 µm inner diameter, 85 cm plain capillary with an electrolyte buffer of 100 mM tricine pH 8.0 for 20 minutes.

The fluorescent peaks were read at 503 and 519 nm with a xenon flash lamp. Distinct peaks are visible for antibody and for antibody antigen complexes. The samples were also run under the conditions described above, on Supleco hydrophilic "P" coated capillaries and J&W hydrophilic coated capillaries.

Clinical Sample Assay

A blood sample from a multiple sclerosis patient treated with Betaseron™ is drawn after administration of drug. The sample is diluted 1 to 10 into phosphate buffered saline, and pre-incubated at 37° for four hours. Monoclonal antibody A7 labeled with B or R phycoerythrin is added at a concentration of 500 ng/ml and further incubated for one hour at 37°.

An external control of Betaseron/antibody complex at 500 ng/ml concentration is used. Samples are resolved by capillary electrophoresis on an AMS 2000 instrument. Electrophoresis is run according to the following conditions: injection from 100 µl sample (50 ng labeled antibody) for 10 secs. at 0.5 bar; separation at 500 V/cm in a 25 µm inner diameter, 50 cm Supleco hydrophilic "P" coated capillaries with an electrolyte buffer of 50 mM tricine, pH 7.2 for 10 minutes.

The fluorescent peaks are read at 575 nm (with a xenon flash lamp or laser excitation). Distinct peaks are visible for antibody and for antibody antigen complexes.

II. Analysis of Glycosylated Hemoglobin in Blood

Test Assay

Blood was drawn from a human volunteer. The sample was assayed with or without anticoagulants. 50 µl of blood was used. The cells were separated from plasma by centrifugation at 1000×G, for 10 minutes at 20° C. The red cells were lysed by resuspension in 400 µl of a chaotropic lysis solution (Helena Laboratories) for 10 minutes at 20° C. The lysate was then diluted 1:10 with phosphate buffered saline.

Monoclonal antibody A1C (mouse anti-human hemoglobin A1C from Fitzgerald Industries, Int'l) was labeled with FITC. The antibody is specific for human hemoglobin A1C. The antibody was suspended in PBS buffer at a concentration of 540 ng/µl. The antibody was added to the cell lysate at a 1 to 1 ratio, and incubated overnight at 37° C.

Samples were resolved by capillary electrophoresis on an AMS 2000 instrument. Electrophoresis was run according to the following conditions: injection from 100 µl sample (~9 nl injected, ~4.9 ng labeled antibody) for 15 secs. at 0.5 bar; separation at 290–350 V/cm in a 50 µm inner diameter, 85 cm plain capillary with an electrolyte buffer of 50 mM tricine, pH 7.2 for 10 minutes.

The fluorescent peaks were read at 519 nm with a xenon flash lamp. Distinct peaks were visible for antibody and for antibody antigen complexes.

III. Creatine Kinase MB Fraction Analysis

Calibration Assay

A reaction mix of 3 mg/ml creatine kinase MB and 10% human serum in phosphate buffered saline (PBS) was pre-incubated at 37° C. overnight. 11 mg/ml of monoclonal anti-creatine kinase MB, from Omega Biologics, labeled with FITC was added, and the reaction mix further incubated for 1 hour at 37°.

Using DB-17 and DB-1 coated capillaries, sensitive separations have been obtained in about 30 minutes. Using 25 µm inner diameter 50 cm capillaries, and 50 mM tricine buffer at pH 7.2 with an unexpectedly long injection (15 seconds at 500 mb) resulted in separation within 2.5 minutes. Other separations in 100 to 180 mM sodium borate in plain fused capillaries 75 µm×70 cm gave interesting profiles in less than ten minutes. Samples were resolved by capillary electrophoresis on an AMS 2000 instrument. Electrophoresis was run according to the following conditions: injection from 100 µl sample (10 µl injected, 10 ng labeled antibody) for 15 secs. at 0.5 bar; separation at 600 V/cm in a 25 µm inner diameter, 50 cm DB-17 or DB-1 capillary with an electrolyte buffer of 50 mM tricine, pH 7.2 for 2.5 minutes. Alternatively, electrophoresis was run with injection from 100 µl sample (10 µl injected, 10 ng labeled antibody) for 10 secs. at 0.2 bar; separation at 350 V/cm in a 75 µm inner diameter, 70 cm plain capillary with an electrolyte buffer of 100–180 mM NaBorate, pH 8.3 for 10 minutes.

The fluorescent peaks were read at 519 nm with a xenon flash lamp. Distinct peaks were visible for antibody and for antibody antigen complexes.

It is evident from the above results that the subject invention provides a simple, rapid method for the detection of analytes in biological samples.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for the detection and quantitation of a protein analyte in a physiological sample, said method comprising:

adding a monoclonal antibody to said physiological sample that contains said protein analyte wherein the antibody specifically binds to the protein analyte and wherein the antibody is labeled with a fluorescent marker molecule;

incubating said monoclonal antibody/physiological sample mixture to allow for the formation of complexes between said monoclonal antibodies and said protein analyte;

separating said complexes from any uncomplexed monoclonal antibodies and any uncomplexed protein analyte using capillary electrophoresis, wherein said capillary electrophoresis is performed using Tricine as the buffer; and, detecting and quantitating said protein analyte by comparing the amount of said monoclonal antibody/protein analyte complexes formed versus the amount of said uncomplexed monoclonal antibodies.

2. A method according to claim 1, wherein said physiological sample is blood or a derivative thereof.

3. A method according to claim 2, wherein said fluorescent marker molecule is chosen from the group consisting of fluorescein isothiocyanate, rhodamine, phycoerythrin and allophycocyanin.

4. A method according to claim 3, wherein said protein analyte is β-interferon.

5. A method according to claim 3, wherein said protein analyte is hemoglobin.

6. A method according to claim 3, wherein said protein analyte is creatine kinase MB.

\* \* \* \* \*